US012333734B2

United States Patent
Pal et al.

(10) Patent No.: US 12,333,734 B2
(45) Date of Patent: Jun. 17, 2025

(54) SYSTEM AND METHOD FOR IMAGING OF LOCALIZED AND HETEROGENEOUS DYNAMICS USING LASER SPECKLE

(71) Applicant: Tata Consultancy Services Limited, Mumbai (IN)

(72) Inventors: Parama Pal, Bangalore (IN); Earu Banoth, Bangalore (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 706 days.

(21) Appl. No.: 17/687,889

(22) Filed: Mar. 7, 2022

(65) Prior Publication Data

US 2022/0343510 A1 Oct. 27, 2022

(30) Foreign Application Priority Data

Mar. 9, 2021 (IN) .............................. 202121009917

(51) Int. Cl.
*G06T 7/174* (2017.01)
*G06T 3/4007* (2024.01)

(52) U.S. Cl.
CPC ............ *G06T 7/174* (2017.01); *G06T 3/4007* (2013.01); *G06T 2207/10016* (2013.01); *G06T 2207/10056* (2013.01)

(58) Field of Classification Search
CPC .................. G06T 7/174; G06T 3/4007; G06T 2207/10016; G06T 2207/10056
See application file for complete search history.

(56) References Cited

U.S. PATENT DOCUMENTS 9,664,606 B2 * 5/2017 Hajjarian ............... G01N 11/02
2017/0053178 A1 * 2/2017 Robles-Kelly ............ G06T 7/90
(Continued)

FOREIGN PATENT DOCUMENTS

| CN | 102509263 A | 6/2012 |
|---|---|---|
| CN | 110823812 A | 2/2020 |
| JP | 2017-501385 A | 1/2017 |

OTHER PUBLICATIONS

Badon et al., "Distortion matrix concept for deep optical imaging in scattering media," (2020).
(Continued)

*Primary Examiner* — Pinalben Patel
(74) *Attorney, Agent, or Firm* — Finnegan, Henderson, Farabow, Garrett & Dunner, LLP

(57) ABSTRACT

This disclosure relates generally to speckle image analysis, and, more particularly, to a system and method for imaging of localized and heterogenous dynamics using laser speckle. Existing speckle analysis techniques do not offer the capability to achieve both the dynamic phenomenon which carries over a specific time duration and localizing the extent of the activity at a single, chosen instant of time simultaneously. The present disclosure records an image stack consisting of N speckle images sequentially over a period, divides the image stack into a spatial window and a temporal window, converts the speckle intensity data comprised in the spatial window into a column vector. Construct a diagonal matrix and extract a singular value from the diagonal matrix, then defines a speckle intensity correlation metric using the plurality of singular values, defines a speckle activity and generates a speckle contrast image by graphically plotting the speckle activity values.

9 Claims, 12 Drawing Sheets

(56) References Cited

U.S. PATENT DOCUMENTS

2022/0012861 A1* 1/2022 Cohen .................... G06T 7/001
2022/0358646 A1* 11/2022 Ryan ..................... G06N 20/10
2022/0381697 A1* 12/2022 Atkins ................. G06T 7/0012

OTHER PUBLICATIONS

Mozumi et al., "Singular value decomposition filtering in high-frame-rate cardiac vector flow imaging," Bulletin of Electrical Engineering and Informatics, 9(1):171-179 (2020).

Sagawa et al., "Dense Pixel-wise Micro-motion Estimation of Object Surface by using Low Dimensional Embedding of Laser Speckle Pattern," (2020).

Stoykova et al., "Performance of intensity-based non-normalized pointwise algorithms in dynamic speckle analysis," (2015).

Stoykova et al., "Dynamic speckle analysis with smoothed intensity-based activity maps," Optics and Lasers in Engineering, 93:55-65 (2017).

* cited by examiner

SYSTEM AND METHOD FOR IMAGING OF LOCALIZED AND HETEROGENEOUS DYNAMICS USING LASER SPECKLE

PRIORITY CLAIM

This U.S. patent application claims priority under 35 U.S.C. § 119 to: India Application No. 202121009917, filed on Mar. 9, 2021. The entire contents of the aforementioned application are incorporated herein by reference.

TECHNICAL FIELD

This disclosure relates generally to speckle image analysis, and more particularly to a system and method for imaging of localized and heterogenous dynamics using laser speckle.

BACKGROUND

Laser Speckle Imaging (LSI) is a technique that is used for full-field imaging of blood flow. The technique analyzes fluctuations in a dynamic speckle pattern to detect the movement of particles. The term 'speckle' refers to the characteristic graininess that is observed when illuminating a diffusively reflective object with coherent light. These fluctuating, grainy patterns are typically associated with light that is back scattered from the target surface's inherent microscopic facets and irregularities. A multitude of speckle processing techniques have been developed, either to eliminate them for improving image quality or analyze them for extracting information regarding local scatterers in the target. Further speckle patterns comprise of a summation of field components, each having either a random phase or amplitude or both.

Dynamic speckle analysis is a non-destructive, non-invasive method for observing various physical and biological activities that demonstrate time-dependent variations. Examples of such activities include biological phenomena such as blood flow in various organ systems, degradation due to external stimuli in fruits and vegetables, bacterial activity in fresh produce as well as non-biological phenomena such as the onset of corrosion in metals and drying of paint. Essentially, the transient changes in recorded speckle images of the target object act as a signature of its surface condition because of deformations or local activity. Further, when tracking dynamic changes specifically, a time sequence of speckle images is recorded for the duration corresponding to whatever activity (biological, corrosion, etc.) is to be monitored or assessed. The strength of the activity within the object the extent by which the speckle patterns vary, which is characterized accordingly through locally as well as globally defined correlation parameters.

Some of the existing notable numerical techniques include calculating correlation coefficients, inertial moments, smoothing of intensity-based activities and absolute value of differences. Further, numerous graphical methods have also been developed which typically generate two-dimensional speckle contrast 'maps' to facilitate easier visualization of processes undergone by the target object. However, in many cases, current technologies/existing algorithms for analyzing speckle images suffer from poor contrast and existing speckle analysis techniques do not offer the capability to achieve both the dynamic phenomenon which carries over a specific time duration and localizing the extent of the activity at a single, chosen instant of time simultaneously. Further, previously reported/existing methods analyze time series of images to deduce specular activity and calculate a single parameter over the entire image thereby yielding only temporal information.

SUMMARY

Embodiments of the present disclosure present technological improvements as solutions to one or more of the above-mentioned technical problems recognized by the inventors in conventional systems. For example, in one embodiment, a method for imaging of localized and heterogenous dynamics using laser speckle is provided. The method includes recording, via one or more hardware processors, an image stack consisting of N speckle images, wherein size of each of the speckle image is equal to K*L which is recorded sequentially over a period of time, and wherein K indicates the number of rows and L indicates the number of columns of each of the speckle image; dividing, via the one or more hardware processors, the image stack into a spatial window of size $K_p*L_p$ and a temporal window of $N_p$ around each pixel of each of the speckle image, wherein the spatial window comprises speckle intensity data, and wherein p denotes a subset of K and L comprised in each of the speckle image; converting, via the one or more hardware processors, the speckle intensity data comprised in the spatial window into a column vector $V_p$ of length $K_p*L_p*1$ for each of the speckle image to obtain a plurality of column vectors $V_p$; constructing, via the one or more hardware processors, a diagonal matrix E, based on $K_p$, $N_p$ and $L_p$; extracting, via the one or more hardware processors, a singular value a, from the diagonal matrix EP, wherein a total number of a plurality of singular values a, is represented by min $(K_p L_p V_p)$; defining, via the one or more hardware processors, a speckle intensity correlation metric (CM) using the plurality of singular values $\sigma_1$:

$$CM = \frac{\sigma_1}{\sum_{i=1}^{i=min(K_p L_p, N_p)} \sigma_i};$$

defining, via the one or more hardware processors, a speckle activity (SA) using the defined speckle intensity correlation metric (CM), wherein a plurality of regions of high activity is represented by high speckle activity (SA) values and a plurality of regions of low activity is represented by low speckle activity (SA) values, wherein the speckle activity (SA) is expressed using the equation:

$$SA = 1 - CM$$

$$SA = 1 - \frac{\sigma_1}{\sum_{i=1}^{i=min(K_p L_p, N_p)} \sigma_i};$$

and generating a speckle contrast image by graphically plotting the speckle activity (SA) values to generate an activity map and performing an interpolation across the activity map to obtain an interpolated activity map.

In another aspect, there is provided a system for imaging of localized and heterogenous dynamics using laser speckle. The system comprises: a memory storing instructions; one or more communication interfaces; and one or more hardware processors coupled to the memory via the one or more communication interfaces, wherein the one or more hardware processors are configured by the instructions to: record an image stack consisting of N speckle images wherein size of each of the speckle image is equal to K*L which is recorded sequentially over a period of time, and wherein K indicates the number of rows and L indicates the number of columns of each of the speckle image. The system further comprises dividing the image stack into a spatial window of size $K_p*L_p$ and a temporal window of $N_p$ around each pixel of each of the speckle image, wherein the spatial window comprises speckle intensity data, and wherein p denotes a subset of K and L values comprised in each of the speckle image; converting the speckle intensity data comprised in the spatial window into a column vector $V_p$ of length $K_p*L_p*1$ for each of the speckle image to obtain a plurality of column vectors $V_p$; constructing a diagonal matrix E, based on $K_p$, $N_p$ and $L_p$; extracting a singular value $\sigma_i$ from the matrix $\Sigma_p$ wherein a total number of a plurality of singular values $\sigma_i$ is represented by min $(K_pL_pV_p)$; defining a speckle intensity correlation metric (CM) using the plurality of singular values $\sigma_1$:

$$CM = \frac{\sigma_1}{\sum_{i=1}^{i=min(K_pL_p,N_p)} \sigma_i};$$

defining a speckle activity (SA) using the defined speckle intensity correlation metric (CM), wherein a plurality of regions of high activity is represented by high speckle activity (SA) values and a plurality of regions of low activity is represented by low speckle activity (SA) values, wherein the speckle activity (SA) is expressed using the equation:

$$SA = 1 - CM$$
$$SA = 1 - \frac{\sigma_1}{\sum_{i=1}^{i=min(K_pL_p,N_p)} \sigma_i};$$

and generate a speckle contrast image by graphically plotting the speckle activity (SA) values to generate an activity map and performing an interpolation across the activity map to obtain an interpolated activity map.

In yet another aspect, there are provided one or more non-transitory machine-readable information storage mediums comprising one or more instructions which when executed by one or more hardware processors cause recording an image stack consisting of N speckle images wherein size of each of the speckle image is equal to K*L which is recorded sequentially over a period of time, and wherein K indicates the number of rows and L indicates the number of columns of each of the speckle image; dividing the image stack into a spatial window of size $K_p*L_p$ and a temporal window of $N_p$ around each pixel of each of the speckle image, wherein the spatial window comprises speckle intensity data, and wherein p denotes a subset of K and L values comprised in each of the speckle image; converting the speckle intensity data comprised in the spatial window into a column vector $V_p$ of length $K_p*L_p*1$ for each of the speckle image to obtain a plurality of column vectors $V_p$; constructing a diagonal matrix E, based on $K_p$, $N_p$ and $L_p$; extracting a singular value a, from the matrix $\Sigma_p$ wherein a total number of a plurality of singular values a, is represented by min $(K_pL_pV_p)$; defining a speckle intensity correlation metric (CM) using the plurality of singular values $\sigma_1$:

$$CM = \frac{\sigma_1}{\sum_{i=1}^{i=min(K_pL_p,N_p)} \sigma_i};$$

defining a speckle activity (SA) using the defined speckle intensity correlation metric (CM), wherein a plurality of regions of high activity is represented by high speckle activity (SA) values and a plurality of regions of low activity is represented by low speckle activity (SA) values, wherein the speckle activity (SA) is expressed using the equation:

$$SA = 1 - CM$$
$$SA = 1 - \frac{\sigma_1}{\sum_{i=1}^{i=min(K_pL_p,N_p)} \sigma_i};$$

and generate a speckle contrast image by graphically plotting the speckle activity (SA) values to generate an activity map and performing an interpolation across the activity map to obtain an interpolated activity map.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
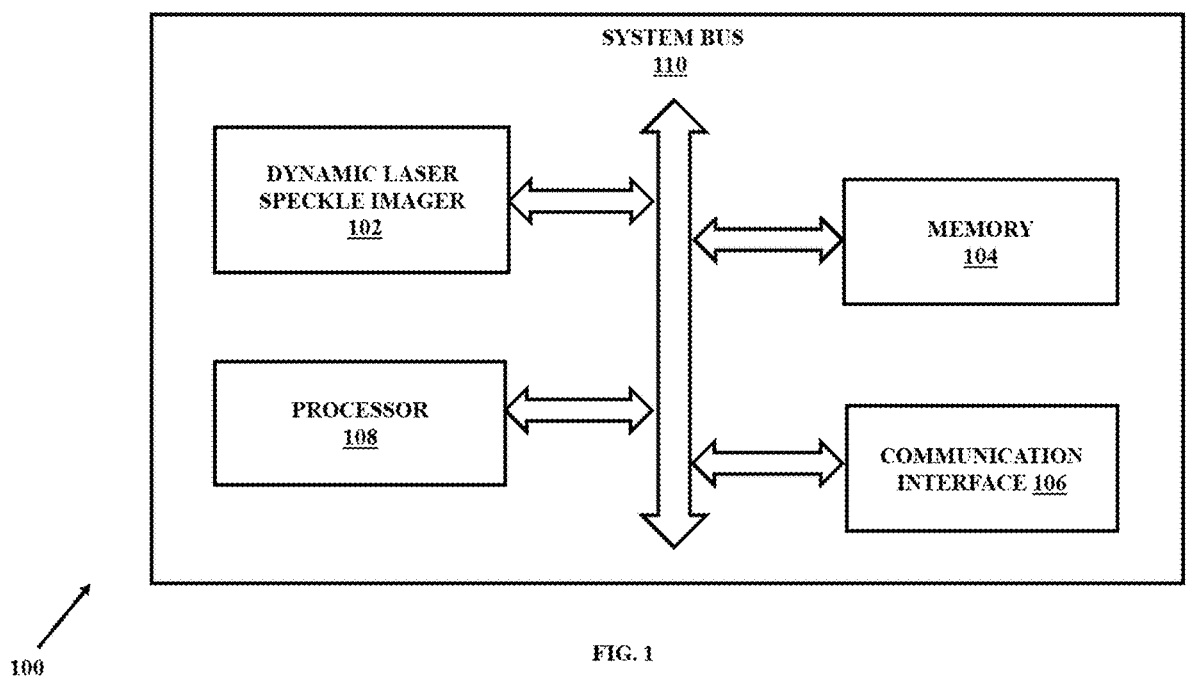
FIG. 1 illustrates an exemplary system, for an imaging of localized and heterogenous dynamics using laser speckle, in accordance with some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

The present disclosure provides a system and method for the imaging of localized and heterogenous dynamics using laser speckle. The present disclosure analyzes how the dynamic phenomenon of speckle imaging is carried over a specific time duration and localizing the extent of the activity at a single, chosen instant of time simultaneously. For instance, consider the corrosion of a metal surface, wherein the extent and rate of corrosion is expected to vary across the surface, the present method can graphically isolate regions of high and low activity (here, rates of corrosion). Additionally, the present disclosure's algorithm involves defining a new correlation measure using mathematical operations that do not use intensity values directly. Further, the present method performs the analysis for larger 'patches' whereas the one of the existing methods for analyzing speckle images involve computations at each pixel of the speckle image.

Referring now to the drawings, and more particularly to FIG. 1 through FIG. 11, where similar reference characters denote corresponding features consistently throughout the figures, there are shown preferred embodiments and these embodiments are described in the context of the following exemplary system and/or method.

FIG. 1 illustrates an exemplary system, for an imaging of localized and heterogenous dynamics using laser speckle, in accordance with some embodiments of the present disclosure. The system 100 includes the dynamic laser speckle imager 102 to solve the imaging of localized and heterogenous dynamics using laser speckle, in accordance with some embodiments of the present disclosure. The dynamic laser speckle imager 102 includes or is otherwise in communication with a memory 104, a communication interface 106, and a processor 108. The memory 104, communication interface 106, and the processor 108 may be coupled by a system bus 110 or a similar mechanism. Although FIG. 1 shows example components of the dynamic laser speckle imager 102, in other implementations, system 100 may contain fewer components, additional components, different components, or differently arranged components than depicted in FIG. 1.

The processor 108 may be implemented as one or more microprocessors, microcomputers, microcontrollers, digital signal processors, central processing units, state machines, logic circuitries, and/or any devices that facilitates in designing polymeric carrier for controlled release of molecules. Further, the processor 108 may comprise a multi-core architecture. Among other capabilities, the processor 108 is configured to fetch and execute computer-readable instructions or modules stored in the memory 104. The processor 108 may include circuitry implementing, among others, audio and logic functions associated with the communication. For example, the processor 108 may include, but are not limited to, one or more digital signal processors (DSPs), one or more microprocessor, one or more special-purpose computer chips, one or more field-programmable gate arrays (FPGAs), one or more application-specific integrated circuits (ASICs), one or more computer(s), various analog to digital converters, digital to analog converters, and/or other support circuits. The processor 108 thus may also include the functionality to encode messages and/or data or information. The processor 108 may include, among other things, a clock, an arithmetic logic unit (ALU) and logic gates configured to support operation of the processor 108. Further, the processor 108 may include functionality to execute one or more software programs, which may be stored in the memory 104 or otherwise accessible to the processor 108.

The memory 104, may store any number of pieces of information, and data, used by the system 100 to implement the functions of the system 100. The memory 104 may include any computer-readable medium known in the art including, for example, volatile memory, such as static random-access memory (SRAM) and dynamic random-access memory (DRAM), and/or non-volatile memory, such as read only memory (ROM), erasable programmable ROM, flash memories, hard disks, optical disks, and magnetic tapes. Examples of volatile memory may include but are not limited to volatile random-access memory (RAM). The non-volatile memory may additionally or alternatively comprise an electrically erasable programmable read only memory (EEPROM), flash memory, hard drive, or the like. The memory 104 may be configured to store information, data, applications, instructions, or the like for enabling the system 100 to carry out various functions in accordance with various example embodiments. Additionally, or alternatively, the memory 104 may be configured to store instructions which when executed by the processor 108 causes the system 100 to behave in a manner as described in various embodiments.

The communication interface(s) 106 can facilitate multiple communications within a wide variety of networks and protocol types, including wired networks, for example, local area network (LAN), cable, etc., and wireless networks, such as Wireless LAN (WLAN), cellular, or satellite. For the purpose, the communication interface (s) 106 may include one or more ports. One or more functionalities of the system 100 and components thereof, is further explained in detail with respect to block diagram described in FIG. 2.

Figure 2:
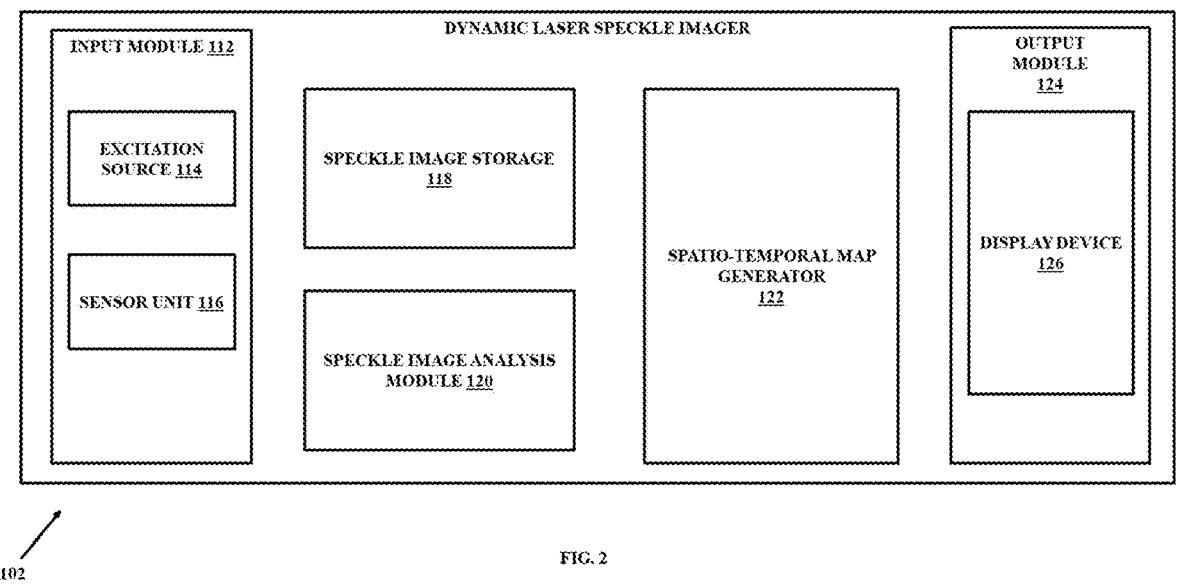
FIG. 2 illustrates an exemplary block diagram of the system, for the imaging of localized and heterogenous dynamics using laser speckle in accordance with some embodiments of the present disclosure.

FIG. 2 illustrates an exemplary block diagram of the system, for the imaging of localized and heterogenous dynamics using laser speckle in accordance with some embodiments of the present disclosure. In an embodiment, the dynamic laser speckle imager 102 comprises of various modules that include an input module 112, a speckle image storage 118, a speckle image analysis module 120, a spatio-temporal map generator 122 and an output module 124. The input module 112 includes an excitation source 114, and a sensor unit 116. The output module 124 includes a display device 126.

Figure 3A:
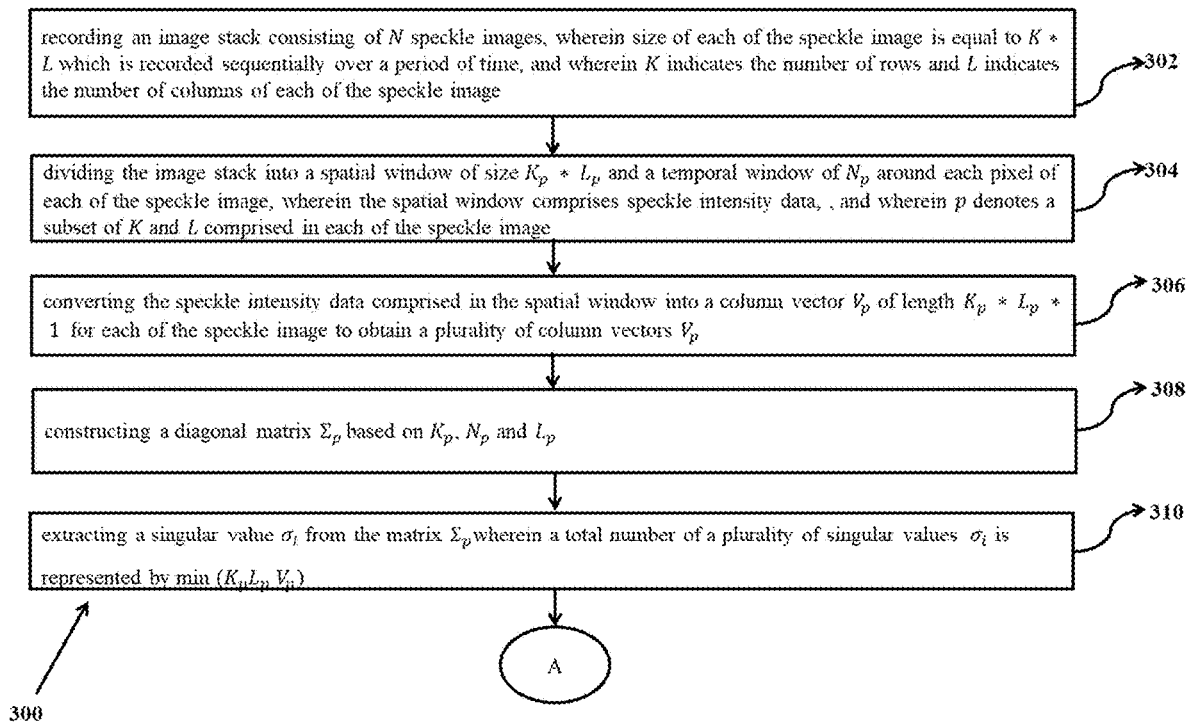
FIGS. 3A and 3B is an exemplary flow diagram, illustrating a method for imaging of localized and heterogenous dynamics using laser speckle, in accordance with some embodiments of the present disclosure.
Figure 3B:
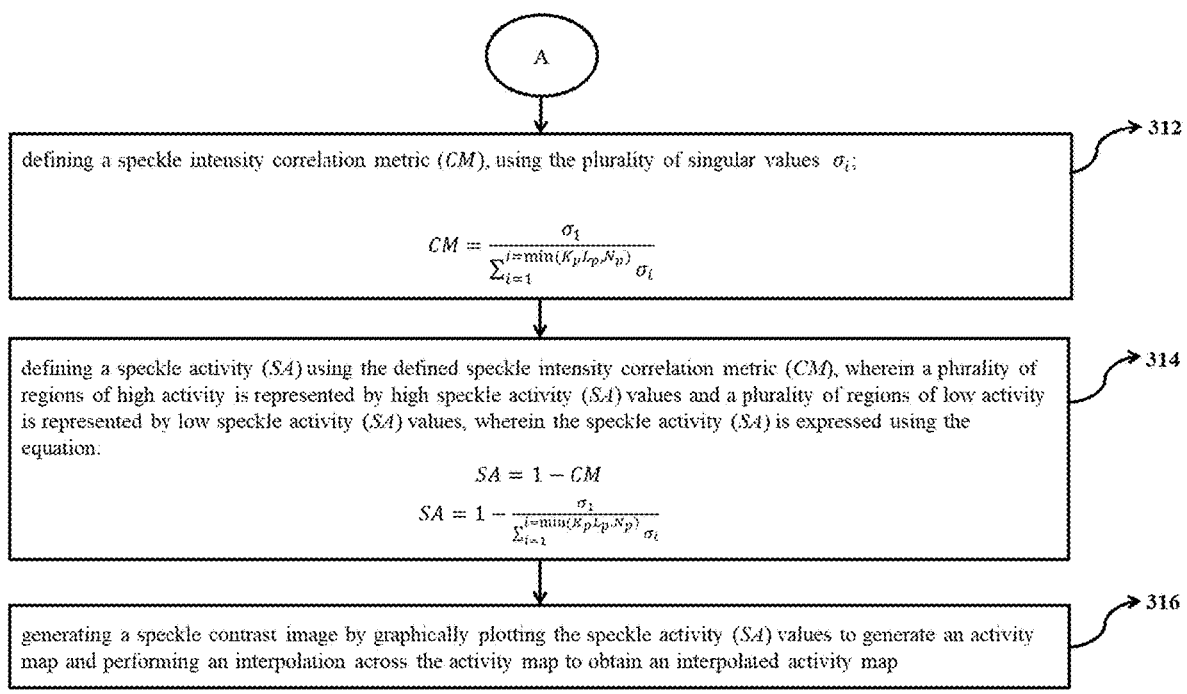

FIGS. 3A and 3B, with reference to FIGS. 1-2, is an exemplary flow diagram 300 illustrating a method for imaging of localized and heterogenous dynamics using laser speckle using the system 100 of FIG. 1 according to some embodiments of the present disclosure. In an embodiment, the system 100 comprises one or more data storage devices or the memory 104 operatively coupled to the one or more processors 108 and is configured to store instructions for execution of steps of the method by the surface crack segmentation unit 102. The steps of the method of the present disclosure will now be explained with reference to the components of the system 100 and the steps 302-316 as depicted in FIGS. 3A-3B, and the flow diagram as depicted in FIGS. 3A and 3B.

Operations of the flowchart, and combinations of operation in the flowchart, may be implemented by various means, such as hardware, firmware, processor, circuitry and/or other device associated with execution of software including one or more computer program instructions. For example, one or more of the procedures described in various embodiments may be embodied by computer program instructions. In an example embodiment, the computer program instructions, which embody the procedures, described in various embodiments may be stored by at least one memory device of a system and executed by at least one processor in the system. Any such computer program instructions may be loaded onto a computer or other programmable system (for example, hardware) to produce a machine, such that the resulting computer or other programmable system embody means for implementing the operations specified in the flowchart. It will be noted herein that the operations of the method 300 are described with help of system 102. However, the operations of the method 300 can be described and/or practiced by using any other system.

The disclosed method 300 relates to the imaging of localized and heterogenous dynamics using laser speckle. At step of the method 302, the one or more hardware processors 108 record an image stack consisting of N speckle images wherein size of each speckle image is equal to K*L which are recorded sequentially over a period of time, and wherein K indicates the number of rows and L indicates the number of columns of each of the speckle image. In an embodiment of the present disclosure, period of time can be of any value which is basically limited by the memory handling capabilities of a processing unit. Basically, period of time of acquisition correlates with the time scales of the dynamics that the user is trying to capture. The present disclosure inspects both the spatial and temporal statistics of the speckle patterns. In an embodiment of the present disclosure, the input module 112 which includes the excitation source 114 and the sensor unit 116 of FIG. 2 is used to record an image stack consisting of N speckle images. The excitation source 114 can include a laser and the sensor unit 116 which is also referred to as an image capturing unit or image sensor. Such image capturing unit or image sensor can include a camera for capturing speckle images. The speckle image storage 118 of FIG. 2 is configured to store the recorded N speckle images/frames for the analysis. In an embodiment of the present disclosure, the speckle image analysis module 120 of FIG. 2 essentially encapsulates the processing algorithm i.e., the patch-wise SVD algorithm, where the patch-wise SVD is being calculated for each patch/sub-region and not the entire frame under consideration. At step of the method 304, the one or more hardware processors 108 divide the image stack into a spatial window of size $K_p*L_p$ and a temporal window of $N_p$ around each pixel of each of the speckle image, wherein the spatial window comprises speckle intensity data, and wherein p denotes a subset of K and L comprised in each of the speckle image. In an embodiment of the present disclosure, the N speckle images are divided into 30 spatial windows. Such division of N speckle images shall not be construed as limiting the scope of the present disclosure. At step of the method 306, the one or more hardware processors 108, convert the speckle intensity data comprised in the spatial window into a column vector $V_p$ of length $K_p*L_p*1$ for each of the speckle image to obtain a plurality of column vectors $V_p$. In an embodiment of the present disclosure, a diagonal matrix $I_p$ of size $K_pL_p*N_p$ is constructed by stacking together all the column vectors $N_p$. Further a real unitary matrix $U_p$ of size $K_pL_p*K_pL_p$ and real unitary matrix $V_p$ of size $N_p*N_p$ are constructed. Further a singular value decomposition (SVD) of matrix $I_p$ is calculated to estimate the correlation between speckle intensities which can be represented as $I_p = U_p \Sigma_p V_p$. At step of the method 308, the one or more hardware processors 108, construct a diagonal matrix $\Sigma_p$ of size $K_pL_p*N_p$. At step of the method 310, the one or more hardware processors 108, extract a singular value $\sigma_i$ from the matrix $\Sigma_p$ wherein a total number of a plurality of singular values $\sigma_i$ is represented by min $(K_pL_pV_p)$. The process of extracting the singular values $\sigma_i$ from the matrix $\Sigma_i$ is represented as the singular value decomposition. At step of the method 312, the one or more hardware processors 108, define a speckle intensity correlation metric (CM) using the plurality of singular values $\sigma_i$:

$$CM = \frac{\sigma_1}{\sum_{i=1}^{i=min(K_pL_p,N_p)} \sigma_i}$$

In the singular value decomposition (SVD) computation, these singular values are arranged in a descending order along the main diagonal, in one example embodiment. The spatio-temporal map generator 122 of FIG. 2 is configured to compute the activity map.

At step of the method 314, the one or more hardware processors 108, define a speckle activity (SA) using the defined speckle intensity correlation metric (CM), wherein a plurality of regions of high activity is represented by high speckle activity (SA) values and a plurality of regions of low activity is represented by low speckle activity (SA) values, wherein the speckle activity (SA) is expressed using the equation:

$$SA = 1 - CM$$

$$SA = 1 - \frac{\sigma_1}{\sum_{i=1}^{i=min(K_pL_p,N_p)} \sigma_i}$$

In an embodiment of the present disclosure, the SA values are a quantified measure of the extent of local 'activity', i.e., the transient changes in the sample (e.g., speckle image). Further, a map of these SA values directly gives us information about localized regions of changes in the sample (e.g., speckle image) and to evaluate the region and an instant of time, where the changes are occurring in the sample (e.g., speckle image), SA values are computed and plotted graphically. Herein the terms "SA values" and "CM values" can be interchangeably used.

At step of the method 316, the one or more hardware processors 108, generate a speckle contrast image by graphically plotting the speckle activity (SA) values (or CM values) to generate an activity map and subsequently perform an interpolation across the generated activity map to obtain an interpolated activity map. The SA is computed for each non-overlapping patch/sub-region. A plot is rendered using these SA/CM values (for each patch) thereby generating the final image (activity map). In an embodiment of the present disclosure, the output module 124 which includes the display device 126 is configured to display the activity map. Here, it is observed that in the case of high speckle intensity correlations, of all the singular values, only a small subset has dominant/significant magnitudes whereas the rest have negligibly small magnitudes, i.e., the plurality of regions with low activity has high intensity correlation metric (CM) values. On the other hand, for low speckle intensity correlations, a higher number of singular values possess significant magnitude i.e., the plurality of regions with high activity comprises low intensity correlation metric (CM) values. In spatial regions corresponding to low activity levels, i.e., where the speckle movements are less, the speckle intensities are highly correlated thereby resulting in a higher value of the ratio of the first singular value $\sigma_1$ to the sum of singular values, i.e., $$\frac{\sigma_1}{\sum_{i=1}^{i=min(K_pL_pN_p)} \sigma_i}.$$

Similarly, at regions of higher activity level, the speckle intensities are mostly uncorrelated due to higher speckle movements. As a result, the aforementioned ratio is relatively small and the speckle activity at that location is quantified to be high. The metric SA (speckle activity which is defined in equation 1) is assigned to each pixel and the value of SA lies between $$\left[\frac{1}{min(K_pL_pN_p)}, 1\right].$$

This 'moving window' operation is performed at each pixel to yield a comprehensive map of the complete speckle activity. In the patch-wise approach, the matrix $I_p$ is generated using non-overlapping sub-regions of the speckle image(s) or speckle patches, each of size $K_pL_p*N_p$. Since a single speckle activity (SA) parameter is computed for the pixels in a given patch, interpolation is performed across the activity map to retain the same spatial resolution as that of the original speckle image.

Figure 4:
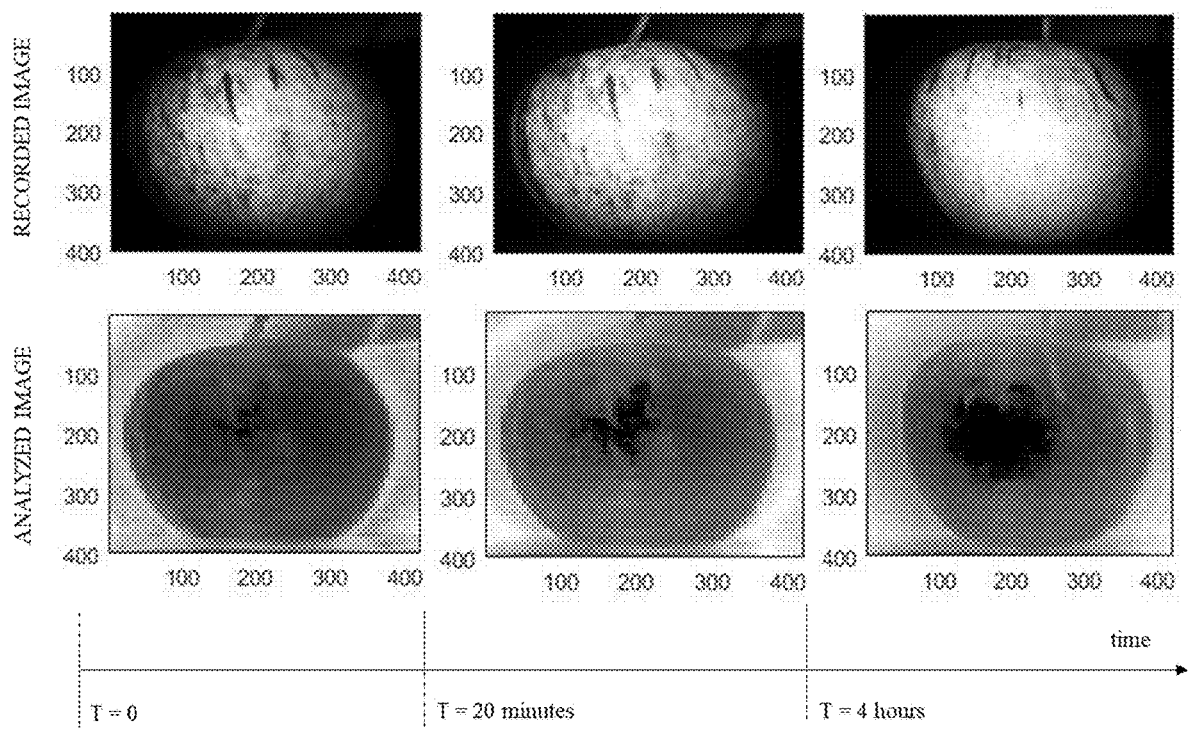
FIG. 4 is a use case illustrating the imaging of localized and heterogenous dynamics using laser speckle, in accordance with some embodiments of the present disclosure.

FIG. 4 is a use case illustrating the imaging of localized and heterogenous dynamics using laser speckle, in accordance with some embodiments of the present disclosure. The speckle pattern was generated by the surface of as 'healthy' apple wherein a small pin prick on the surface is introduced or inflicted. Presumably, this induces damage/bruising inside the apple wherein the degradation is not visible on the surface of the apple but is readily discernible when recorded speckle images are analyzed using the method of the present disclosure. After T=4 hours, a portion of the apple was sliced off, which revealed extensive bruising and was not apparent on the surface as depicted in the recorded image part of FIG. 4. The processed images depicted in analyzed image part of FIG. 4 shows the damage and bruising under the surface which is apparent here. Further the images depicted in FIG. 4 were taken when the apple was still intact.

Figure 5A:
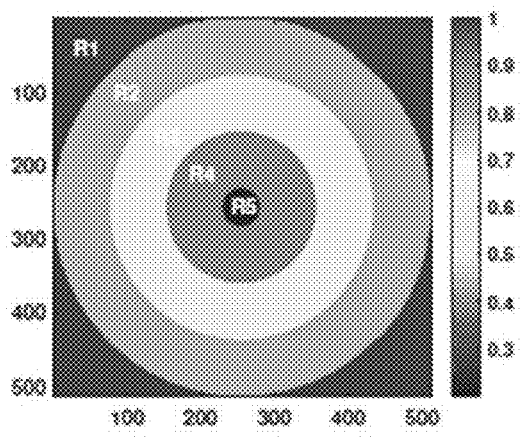
FIGS. 5A and 5B shows a use case example of a simulated speckle correlation map by dividing into the regions and the plot of temporal speckle correlations associated with each region respectively, in accordance with some embodiments of the present disclosure.
Figure 5B:
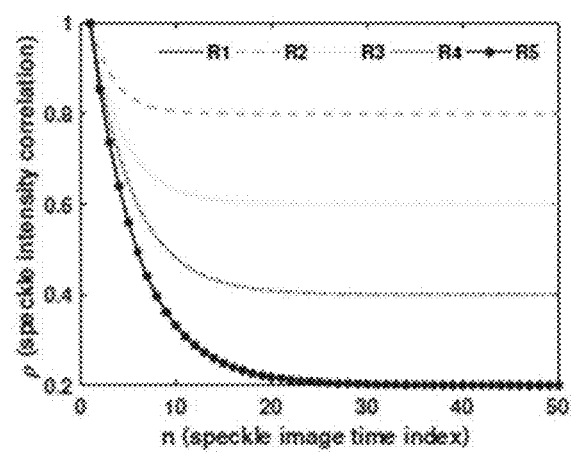

FIGS. 5A and 5B show a use case example of a simulated speckle correlation map by dividing into the regions and the plot of temporal speckle correlations associated with each region respectively, in accordance with some embodiments of the present disclosure. The present disclosure uses simulation of dynamic speckle sequences method (well-known in the prior art) to simulate speckle images with pre-defined spatial as well as temporal correlations. The present disclosure briefly uses I(k,l,n) to represent the intensity of the nth speckle image at pixel (k,l) which is computed as, $$I(k,l,n)=|F^{-1}[H \cdot F[e^{j\varphi(k,l,n)}]]|^2$$

where $k \in [0,K-1], l \in [0,L-1]$; $j=\sqrt{-1}$; F and $F^{-1}$ represents a Fourier and an inverse Fourier transform operations; H represents a low pass filter in the Fourier space which is associated with the circular aperture of a camera lens; $\varphi(k,l,n)$ represents the random phase of the light scattered from the rough surface at the nth frame, K indicates the number of rows and L indicates the number of columns of each of the speckle image. The initial phase distribution $\varphi(k,l,0)$ is simulated as a matrix with uniformly distributed values in the interval $(-\pi,\pi)$. In dynamic speckle simulations, the phase distributions at the nth frame are computed as, $$\varphi(k,l,n)=p(k,l,n-1)+G(k,l,n)\sqrt{Inc(k,l,n-1)-Inc(k,l,n)},$$

where; G(k,l,n) represents a K×L random matrix with Gaussian distributed values having a mean of zero and standard deviation of one; and c(k,l,n) represents the correlation coefficient (which varies both spatially as well as temporally). The matrix G is computed at every nth frame.

In the present disclosure $N_p$=N is considered. A total of N=50 speckle images each of size K×L=512*512 were simulated with an average speckle size (spx) equal to two pixels. Such specification of speckle size (spx) shall not be construed as limiting the scope of the present disclosure. The image area was segmented into five annular rings, within each ring, the temporal speckle correlation decreased at distinct rates. Such segmentation of image area shall not be construed as limiting the scope of the present disclosure. FIG. 5A depicts the image area indicating these regions with speckle correlation values considered at the frame number n=50. The decrease in the temporal speckle correlation associated with each segmented region as a function of the frame number n is plotted as depicted in FIG. 5B. In the present disclosure, the simulated and experimental speckle contrast analyses were performed using MATLAB R2017a on a standard computer with an Intel® i5-6500 processor@ 3.20 GHz and 8 GB RAM.

Figure 6:
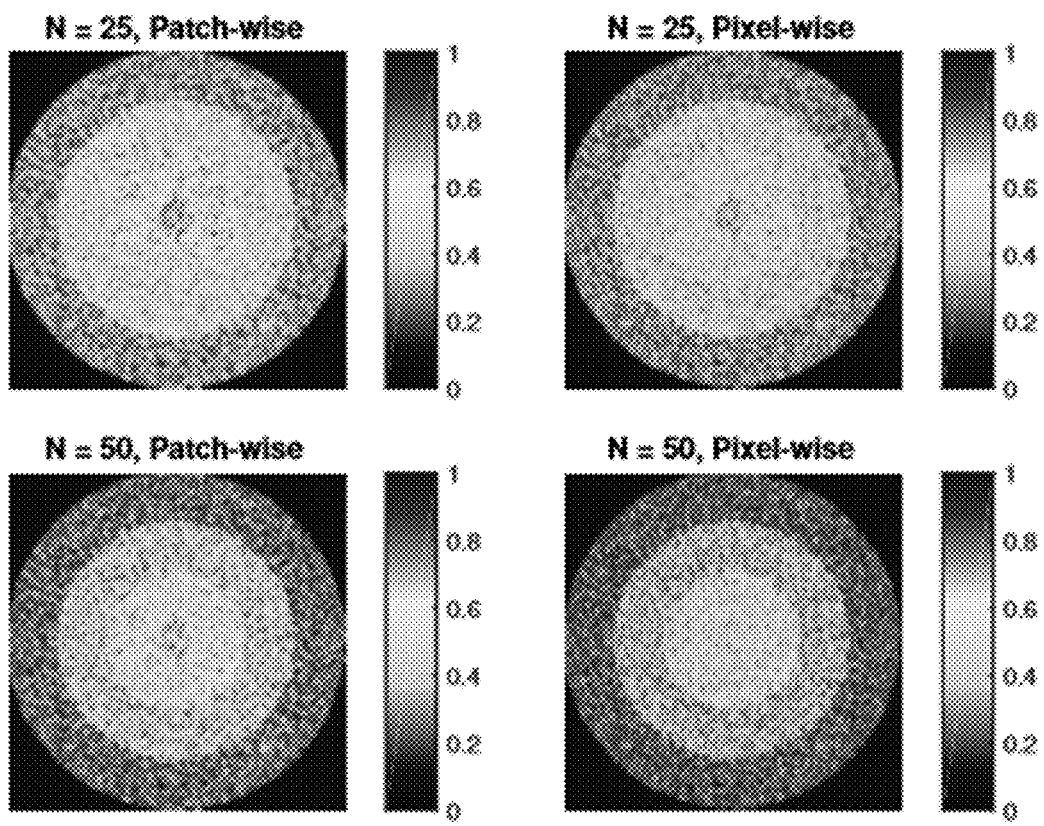
FIG. 6 shows a use case example of a speckle activity map computed using the patch-wise Spatio-Temporal-SVD (singular value decomposition) and the pixel-wise Spatio-Temporal-SVD (ST-SVD) approaches for N=25 and N=50, in accordance with some embodiments of the present disclosure.

FIG. 6 shows a use case example of a speckle activity map computed using the patch-wise Spatio-Temporal-SVD (singular value decomposition) and the pixel-wise Spatio-Temporal SVD (ST-SVD) approaches for N=25 and N=50, in accordance with some embodiments of the present disclosure. The correlation value is evaluated at each pixel and a patch-wise approach wherein the pixel-wise and patch-wise speckle contrast analyses were used to obtain the speckle contrast maps as depicted in FIG. 6 for N=25 and N=50. The window and patch sizes were set to $K_p*L_p$=3×3. The pixel-wise approach for contrast map generation took 27.7 and 48.3 seconds for N=25 and N=50, respectively, and the patch-wise approach performed the same with 2.9 and 5.1 seconds for N=25 and N=50, respectively. Clearly, the patch-wise approach proved to be more computationally efficient than the pixel-wise approach.

Figure 7:
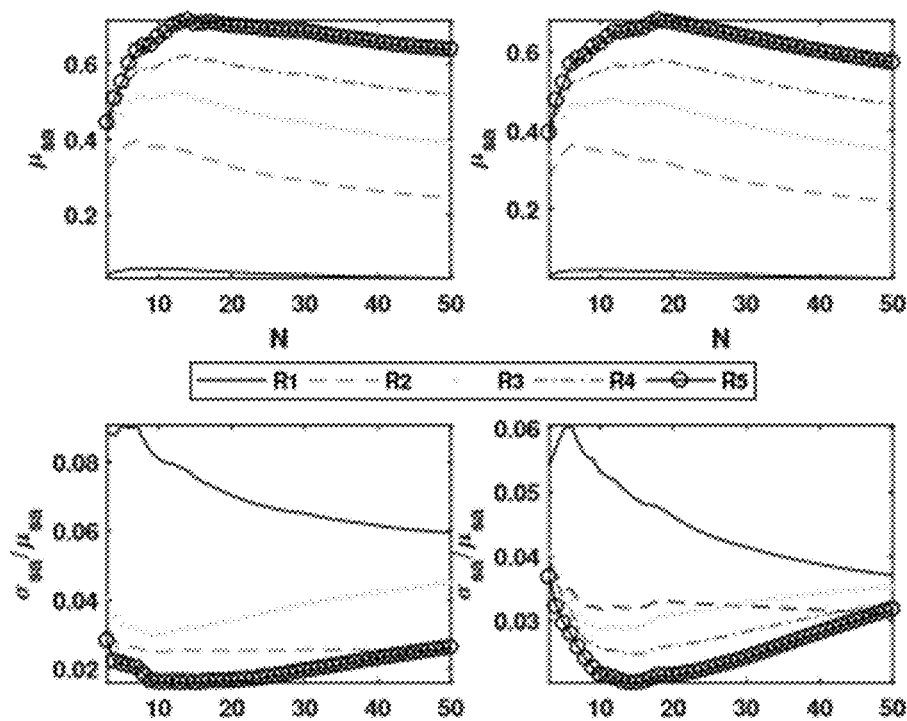
FIG. 7 shows a use case example of the plots of μsa and σsa/μsa associated with the speckle activity map obtained using the patch-wise and pixel-wise approach, in accordance with some embodiments of the present disclosure.

FIG. 7 shows a use case example of the plots of mean ($\mu_{sa}$) and ratio of the variance ($\sigma_{sa}$) to the mean ($\mu_{sa}$) i.e., $\sigma_{sa}/\mu_{sa}$ associated with the speckle activity map obtained using the patch-wise and pixel-wise approach, in accordance with some embodiments of the present disclosure. In conjunction with the FIG. 6, a quantifiable performance measure of the pixel-wise approach and patch-wise approach is given by the noise level of a speckle contrast image which is provided by the ratio of the variance ($\sigma_{sa}$) to the mean ($\mu_{sa}$) of the speckle activity. Further, the ratio of the variance ($\sigma_{sa}$) to the mean ($\mu_{sa}$) of the speckle activity is calculated as a function of N within each distinct region as per FIG. 5A. Further, for the estimated mean values, it can be observed that both the approaches i.e., the pixel-wise approach and the patch-wise approach were able to distinctly identify mean speckle activity within each region even for smaller values of N. However, as the patch-wise approach took lesser time to execute and provided comparable performance to the pixel-wise method.

Figure 8:
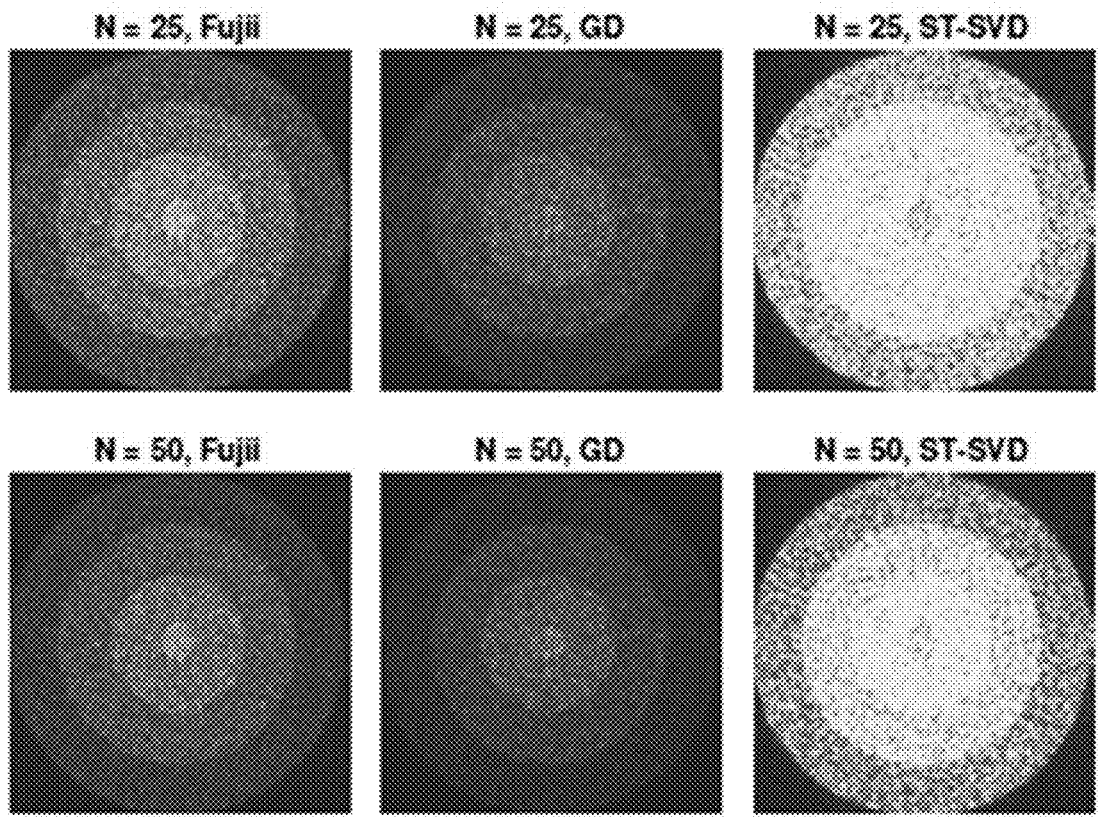
FIG. 8 shows a use case example of the speckle activity maps computed using the Fujii, Generalized Difference (GD) (well-known techniques in the prior art) and the patch-wise ST-SVD method for N=25 and N=50, in accordance with some embodiments of the present disclosure.

FIG. 8 shows a use case example of the speckle activity maps computed using the Fujii, Generalized Difference (well-known techniques in the prior art) and the patch-wise Spatio-Temporal-SVD method for N=25 and N=50, in accordance with some embodiments of the present disclosure. In an embodiment, the performance of the method of the present disclosure, i.e., patch-wise method is compared with two commonly used graphical speckle contrast analysis techniques (well-known in the prior art), namely, the Fujii and the Generalized Difference techniques. For the simulated correlation map shown in FIGS. 5A and 5B, the speckle contrast maps were generated with N=25 and N=50 as depicted in FIG. 8. It is observed that the patch-wise method as described by the present disclosure provides a relatively clearer distinction between areas having different speckle activity rates as compared to the other methods namely, the Fujii and the Generalized Difference techniques.

Figure 9:
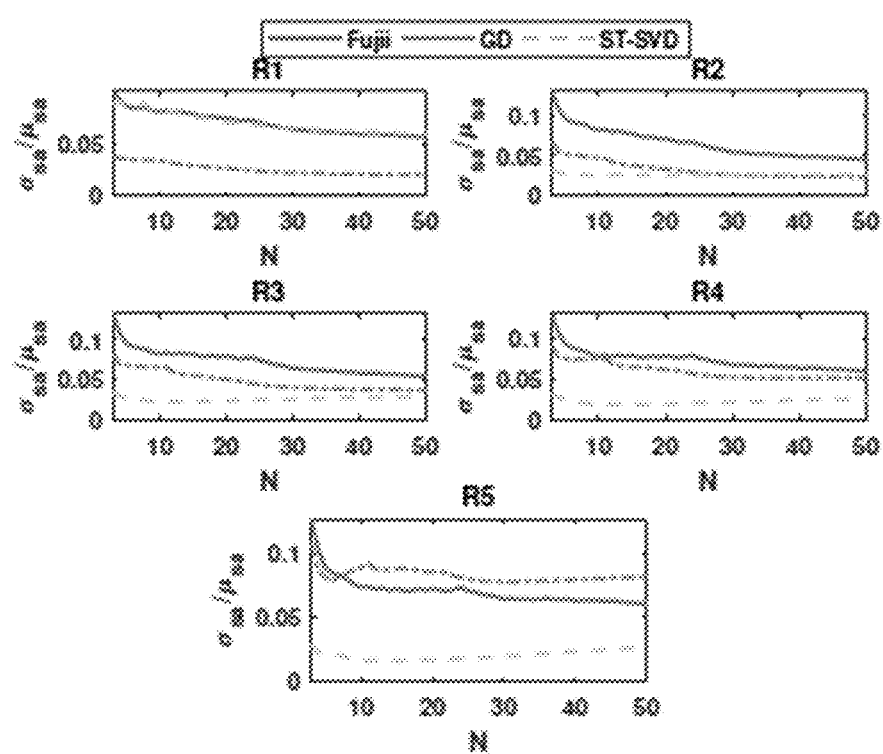
FIG. 9 shows a use case example of the plots of $\sigma_{sd}/\mu_{sa}$ computed within each region of the speckle images in function of N, in accordance with some embodiments of the present disclosure.

FIG. 9 shows a use case example of the plots of $\sigma_{sa}/\mu_{sa}$ computed within each region of the speckle images in function of N, in accordance with some embodiments of the present disclosure. In conjunction with FIG. 8, to validate the observation of FIG. 8, a quantitative comparison of the method of the present disclosure with two commonly used graphical speckle contrast analysis techniques (well-known in the prior art), namely, the Fujii and the Generalized Difference techniques is done by calculating the ratio of the variance ($\sigma_{sa}$) to the mean ($\mu_{sa}$) of the speckle activity as a function of N within each distinct region as per FIG. 5A. FIG. 9 depicts the region-wise ratio as a function of N for all the above-mentioned methods under consideration and shows that the proposed patch-wise SVD method has the lowest ratio and hence offers greater accuracy.

Figure 10:
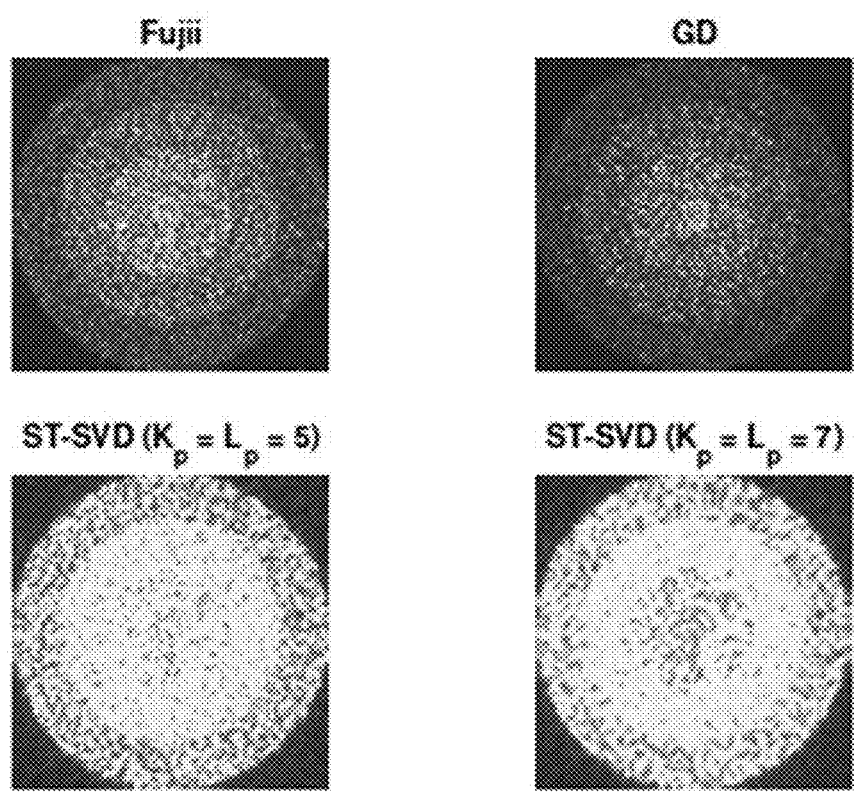
FIG. 10 shows a use case example of the speckle activity maps computed using the Spatio-Temporal-SVD method for simulated dynamic speckle images having speckle size equal to 4 pixels using the Fujii, the Generalized Difference and the ST-SVD method with $K_p=L_p=5$ and $K_p=L_p=7$, in accordance with some embodiments of the present disclosure.

FIG. 10 shows a use case example of the speckle activity maps computed using the Spatio-Temporal-SVD method for simulated dynamic speckle images having speckle size equal to 4 pixels using the Fujii, the Generalized Difference and the ST-SVD method with $K_p=L_p=5$ and $K_p=L_p=7$, in accordance with some embodiments of the present disclosure. The speckle activity maps for simulated dynamic speckle images with an average speckle size equal to 4 pixels as shown in FIG. 10. Such specification of speckle size shall not be construed as limiting the scope of the present disclosure. Intuitively, an increase in the speckle size correlates with an increase in the spatial correlation among pixel intensities, thereby resulting in a decrease of the spatial resolution in the activity map. To compensate for this, the patch size should therefore be increased with an increase in the speckle size in order to capture differing levels of speckle activity within a sub-region, albeit at a lower spatial resolution. It is observed that, for larger speckle sizes as well, the patch-wise SVD method of the present disclosure yields an improved speckle contrast image as compared to the Fujii and the Generalized Difference method.

Figure 11:
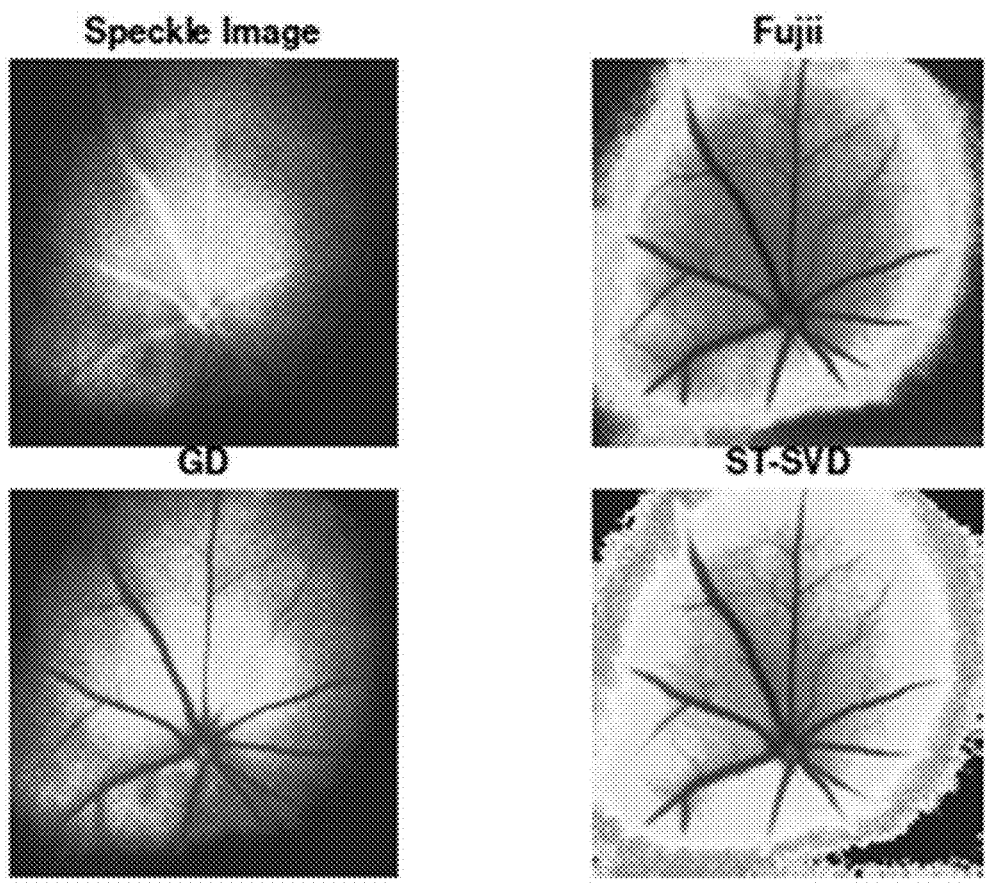
FIG. 11 shows a use case example of the speckle images of a mouse retina recorded using a modified fundus camera, in accordance with some embodiments of the present disclosure.

FIG. 11 shows a use case example of the speckle images of a mouse retina recorded using a modified fundus camera, in accordance with some embodiments of the present disclosure. The method of the present disclosure was applied to synthetic speckle data and further validated the proposed method/algorithm using experimental data that was acquired using a modified fundus camera for detecting changes in the retinal hemodynamics of a rodent model. The speckle image dataset (comprising of a total of thirty images) was analyzed using Fujii, Generalized Difference (well-known techniques in the prior art) and the patch-wise SVD method (with $K_p=L_p=3$) as shown in FIG. 11. The first speckle image in the dataset is shown in the figure for the purpose of illustration. A visual inspection shows the improvement in the speckle contrast of the image obtained with the patch-wise SVD method as compared to the other two methods namely Fujii, Generalized Difference (well-known techniques in the prior-art).

In the present method, the local variations in the speckle intensity are quantified utilizing the dimensionality reduction technique using the singular value decomposition. There exist a few the singular values with the singular values of significant magnitude corresponding to the local speckle activity related intensity fluctuations. By quantifying the spatial variations in the magnitude of these singular values, the spatially varying speckle activity map is generated. A similar approach can be readily used for the purpose of noise cancellation under the assumption that the signal is of lower frequency than the noise. In the case of active noise cancellation, the singular value-based metric can be evaluated at two locations simultaneously, at the region of interest and at a reference region. The reference region is selected such that the signal collected from this region is entirely due to the noise. On the other hand, the signal recorded at the region of interest consist of contribution from the parameter under investigation and noise. Under the assumption that these two regions are subjected to same environment, the noise statistics in the signal recorded at these regions is same. Thus, the subtraction of activity map evaluated at these two locations effectively provides active noise cancellation.

Hence, the present disclosure provides a system and method for imaging of localized and heterogenous dynamics using laser speckle. The present disclosure describes a method for statistically analyzing dynamic speckle patterns by using a singular value decomposition technique. The method of the present disclosure provides the spatial as well as temporal variations of speckle intensity fluctuations by generating two-dimensional activity maps using speckle correlation values. The present disclosure calculates the correlation measures for each patch thereby localizing the information contained within the speckle images. The present disclosure generates 'activity maps' derived from sequentially recorded speckle images of dynamic, heterogenous phenomena, such as blood flow in various organ systems, corrosion in metals, degradation in fruits, amongst others. Further, the method extracts spatio-temporal data by analyzing each speckle image in a patch-wise manner by calculating its singular values, which are indirectly derived from intensity values and not the intensity values themselves. This leads to improved contrast and reduced artifacts in the graphically generated contrast maps.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g., any kind of computer like a server or a personal computer, or the like, or any combination thereof. The device may also include means which could be e.g., hardware means like e.g., an application-specific integrated circuit (ASIC), a field-programmable gate array (FPGA), or a combination of hardware and software means, e.g., an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g., using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor-implemented method, comprising:

recording, via one or more hardware processors, an image stack consisting of N speckle images, wherein size of each of the speckle image is equal to K*L which is recorded sequentially over a period of time, and wherein K indicates the number of rows and L indicates the number of columns of each of the speckle image;

dividing, via the one or more hardware processors, the image stack into a spatial window of size $K_p*L_p$ and a temporal window of $N_p$ around patches of each of the speckle image, wherein the spatial window comprises speckle intensity data, and wherein p denotes a subset of K and L comprised in each of the speckle image;

converting, via the one or more hardware processors, the speckle intensity data comprised in the spatial window into a column vector $V_p$ of length $K_p*L_p*1$ for each of the speckle image to obtain a plurality of column vectors $V_p$;

constructing, via the one or more hardware processors, a diagonal matrix $\Sigma_p$ based on $K_p$, $N_p$ and $L_p$;

extracting, via the one or more hardware processors, a singular value $\sigma_i$ from the diagonal matrix $\Sigma_p$, wherein a total number of a plurality of singular values $\sigma_i$ is represented by min $(K_p L_p V_p)$;

defining, via the one or more hardware processors, a speckle intensity correlation metric (CM) using the plurality of singular values $\sigma_1$:

$$CM = \frac{\sigma_1}{\sum_{i=1}^{i=min(K_p L_p, N_p)} \sigma_i};$$

defining, via the one or more hardware processors, a speckle activity (SA) using the defined speckle intensity correlation metric (CM), wherein a plurality of regions of high activity is represented by high speckle activity (SA) values and a plurality of regions of low activity is represented by low speckle activity (SA) values, wherein the speckle activity (SA) is expressed using the equation:

$$SA = 1 - CM$$

$$SA = 1 - \frac{\sigma_1}{\sum_{i=1}^{i=min(K_pL_p,N_p)} \sigma_i};$$

generating, via the one or more hardware processors, a speckle contrast image by graphically plotting the speckle activity (SA) values to generate an activity map and performing an interpolation across the activity map to obtain an interpolated activity map.

2. The method of claim 1, wherein the plurality of regions with high activity comprises low intensity correlation metric (CM) values and the plurality of regions with low activity have high intensity correlation metric (CM) values.

3. The method of claim 1, wherein the interpolation is performed across the activity map to retain the same spatial resolution for all N speckle images comprised in the image stack.

4. A system, comprising:

a memory storing instructions;

one or more communication interfaces; and one or more hardware processors coupled to the memory via the one or more communication interfaces, wherein the one or more hardware processors are configured by the instructions to:

record an image stack consisting of N speckle images wherein size of each of the speckle image is equal to K*L which is recorded sequentially over a period of time, and wherein K indicates the number of rows and L indicates the number of columns of each of the speckle image;

divide the image stack into a spatial window of size $K_p*L_p$ and a temporal window of Np around patches of each of the speckle image, wherein the spatial window comprises speckle intensity data, and wherein p denotes a subset of K and L values comprised in each of the speckle image;

convert the speckle intensity data comprised in the spatial window into a column vector $V_p$ of length $K_p*L_p*1$ for each of the speckle image to obtain a plurality of column vectors $V_p$;

constructs a diagonal matrix $\Sigma_p$ based on $K_p$, $N_p$ and $L_p$;

extracts a singular value $\sigma_i$ from the matrix $\Sigma_p$ wherein a total number of a plurality of singular values $\sigma_i$ is represented by min $(K_pL_p, V_p)$;

define a speckle intensity correlation metric (CM) using the plurality of singular values $\sigma_i$:

$$CM = \frac{\sigma_1}{\sum_{i=1}^{i=min(K_pL_p,N_p)} \sigma_i};$$

define a speckle activity (SA) using the defined speckle intensity correlation metric (CM), wherein a plurality of regions of high activity is represented by high speckle activity (SA) values and a plurality of regions of low activity is represented by low speckle activity (SA) values, wherein the speckle activity (SA) is expressed using the equation:

$$SA = 1 - CM$$

$$SA = 1 - \frac{\sigma_1}{\sum_{i=1}^{i=min(K_pL_p,N_p)} \sigma_i};$$

generate a speckle contrast image by graphically plotting the speckle activity (SA) values to generate an activity map and performing an interpolation across the activity map to obtain an interpolated activity map.

5. The system of claim 4, wherein the plurality of regions with high activity comprises low intensity correlation metric (CM) values and the plurality of regions with low activity have high intensity correlation metric (CM) values.

6. The system of claim 4, wherein the interpolation is performed across the activity map to retain the same spatial resolution for all N speckle images comprised in the image stack.

7. One or more non-transitory machine-readable information storage mediums comprising one or more instructions which when executed by one or more hardware processors cause:

recording an image stack consisting of N speckle images, wherein size of each of the speckle image is equal to K*L which is recorded sequentially over a period of time, and wherein K indicates the number of rows and L indicates the number of columns of each of the speckle image;

dividing the image stack into a spatial window of size $K_p*L_p$ and a temporal window of $N_p$ around patches of each of the speckle image, wherein the spatial window comprises speckle intensity data, and wherein p denotes a subset of K and L comprised in each of the speckle image;

converting the speckle intensity data comprised in the spatial window into a column vector $V_p$ of length $K_p*L_p*1$ for each of the speckle image to obtain a plurality of column vectors $V_p$;

constructing a diagonal matrix $\Sigma_p$ based on $K_p$, $N_p$ and $L_p$;

extracting a singular value $\sigma_i$ from the diagonal matrix $\Sigma_p$, wherein a total number of a plurality of singular values $\sigma_i$ is represented by min $(K_pL_pV_p)$;

defining a speckle intensity correlation metric (CM) using the plurality of singular values $\sigma_1$:

$$CM = \frac{\sigma_1}{\sum_{i=1}^{i=min(K_pL_p,N_p)} \sigma_i};$$

defining a speckle activity (SA) using the defined speckle intensity correlation metric (CM), wherein a plurality of regions of high activity is represented by high speckle activity (SA) values and a plurality of regions of low activity is represented by low speckle activity (SA) values, wherein the speckle activity (SA) is expressed using the equation:

$$SA = 1 - CM$$

$$SA = 1 - \frac{\sigma_1}{\sum_{i=1}^{i=min(K_pL_p,N_p)} \sigma_i};$$

and generating a speckle contrast image by graphically plotting the speckle activity (SA) values to generate an activity map and performing an interpolation across the activity map to obtain an interpolated activity map.

8. The one or more non-transitory machine readable information storage mediums of claim 7, wherein the plurality of regions with high activity comprises low intensity correlation metric (CM) values and the plurality of regions with low activity have high intensity correlation metric (CM) values.

9. The one or more non-transitory machine readable information storage mediums of claim 7, wherein the interpolation is performed across the activity map to retain the same spatial resolution for all N speckle images comprised in the image stack.

* * * * *